US011090317B2

(12) United States Patent
Poras et al.

(10) Patent No.: US 11,090,317 B2
(45) Date of Patent: Aug. 17, 2021

(54) AMINOPHOSPHINIC DERIVATIVES FOR PREVENTING AND TREATING EYE INFLAMMATION

(71) Applicant: PHARMALEADS, Paris (FR)

(72) Inventors: Hervé Poras, Villepreux (FR); Michel Wurm, Royat (FR); Stéphane Melik Parsadaniantz, Nogent sur Marne (FR); Annabelle Reaux-Le Goazigo, Maison Alfort (FR)

(73) Assignee: Pharmaleads, Paris (FR)

( * ) Notice: Subject to any disclaimer, the term of this patent is extended or adjusted under 35 U.S.C. 154(b) by 190 days.

(21) Appl. No.: 16/491,024

(22) PCT Filed: Mar. 9, 2018

(86) PCT No.: PCT/FR2018/050545
§ 371 (c)(1),
(2) Date: Sep. 4, 2019

(87) PCT Pub. No.: WO2018/162860
PCT Pub. Date: Sep. 13, 2018

(65) Prior Publication Data
US 2021/0213036 A1 Jul. 15, 2021

(30) Foreign Application Priority Data

Mar. 9, 2017 (FR) ...................................... 1751912
Sep. 28, 2017 (FR) ...................................... 1759005

(51) Int. Cl.
| | |
|---|---|
| *A61K 31/662* | (2006.01) |
| *A61P 27/02* | (2006.01) |
| *A61P 29/00* | (2006.01) |
| *A61K 47/40* | (2006.01) |
| *A61K 9/00* | (2006.01) |

(52) U.S. Cl.
CPC .......... *A61K 31/662* (2013.01); *A61K 9/0048* (2013.01); *A61K 47/40* (2013.01); *A61P 27/02* (2018.01); *A61P 29/00* (2018.01)

(58) Field of Classification Search
CPC .... A61K 31/662; A61K 47/40; A61K 9/0048; A61P 27/02; A61P 29/00
USPC ....................................................... 514/119
See application file for complete search history.

(56) References Cited

U.S. PATENT DOCUMENTS

| | | | |
|---|---|---|---|
| 6,518,260 B1 | 2/2003 | Fournie-Zaluski et al. | |
| 8,703,747 B2 * | 4/2014 | Roques ................... | A61K 39/08 514/121 |
| 2009/0111794 A1 | 4/2009 | Bacani et al. | |
| 2011/0124601 A1 | 5/2011 | Roques et al. | |
| 2018/0344753 A1 | 12/2018 | Poras et al. | |

OTHER PUBLICATIONS

Bonnard, E., et al, "Long-lasting Oral Analgesic Effects of N-protected Aminophosphinic Dual ENKephalinase Inhibitors (DENKIs) in Peripherially Controlled Pain", Pharamacology Research & Perspectives, vol. 3, No. 2 (Mar. 1, 2015).
Tholander, F. et al, "Structure-Based Dissection of the Active Site Chemistry of Leukotriene A4 Hydrolase: Implications for M1 Aminopeptidases and Inhibitor Design", Chemistry and Biology, Current Biology, London, GB, vol. 15, No. 9, (Sep. 22, 2008).
Hassan, A., et al., "Inflammation of the Rat Paw Enhances Axonal Transport of Opiod Receptors in the Sciatic Nerve and Increases Their Density in the Inflamed Tissue," Neuroscience, vol. 55, No. 1, Jan. 5, 1983, pp. 185-195.
Machelska, H., "Targeting of opiod-producing leukocytes for pain control," Scinence Direct, Neuropeptides 41, Feb. 26, 2007, pp. 355-363.
Gabrilovac, J., et al., "Expression of CD13/aminopeptidas N and CD10/neutral endopeptidase on cultured human keratinocytes," Scinence Direct, Immunology Letters 91, Jul. 3, 2003, pp. 39-47.
Rittner, H., et al., "Opioid Peptide-expressing Leukocytes," Anesthesiology, vol. 95, No. 2, Aug. 2001, pp. 500-508.
Wenk, H., et al., "Effect of morphone sulphate eye drops on hyperalgesia in the rat cornea," International Association for the Study of Pain, Pain 105, Oct. 28, 2002, 455-465.
Hughes, J., et al., "Identification of two related pentapeptides from the brain with potent opiate agonist activity," Nature vol. 258, Dec. 18, 1975, pp. 577-580.
Lord, J., et al., "Endogenous opioid peptides: multiple agonists and receptors," Nature vol. 267, Jun. 9, 1977, pp. 495-499.
Waksman, G., et al., "Autoradiographic comparison of the distribution of the neutral endopeptidas "enkephalinase" and of μ and δ opioid receptors in rat brain," Proc. Natl. Acad. Sci., vol. 83, Oct. 7, 1985, pp. 1523-1527.
Malfroy, B., et al., "High-affinity enkephalin-degrading peptidase in brain is increased after morphine," Nature vol. 276, Nov. 30, 1978, pp. 523-526.
Waksman, G., et al., "In Vitro and In Vivo Effects of Kelatorphan on Enkephalin Metabolism in Rodent Brain," European Journal of Pharmacology, vol. 117 (May 20, 1985, pp. 233-243.
Roques, B., et al., Neutral Endopeptidase 24.11: Structure, Inhibition, and Experimental and Climincal Pharmacology, Pharamcological Reviews, vol. 45, No. 1, 1993, pp. 87-146.

(Continued)

*Primary Examiner* — Kristin A Vajda
(74) *Attorney, Agent, or Firm* — Harness, Dickey & Pierce, PLC (57) ABSTRACT

The disclosure relates to compounds of formula (I): R1-NH—CH(R2)-P(=O)(OH)—CH2-C(R3)(R4)-CONH—C(R5)(R6)-COOR7, where R1 to R7 are as defined in the claims, for use of same in the treatment and/or prevention of ocular inflammation, and more particularly for improving the process of ocular healing. Thus, the compounds of formula (I) are used, in particular, to prevent neovascularisation, or to prevent or treat an ocular inflammation linked to a keratitis, scleritis, episcleritis, uveitis, cataract, synechia, macular oedema, detachment of the retina, ocular hypertension and degeneration of the optical nerve caused by glaucoma.

20 Claims, 7 Drawing Sheets

(56) References Cited

OTHER PUBLICATIONS

Chen, H., et al., "Phosphinic Derivatives as New Dual Enkephalin Degrading Enzyme Inhibitors: Synthesis, Biological Properties, and Antinociceptive Activities," J. Med. Chem. vol. 43, Sep. 21, 1999, pp. 1398-1408.
Chen, H., et al., "Long Lasting Antinociceptive Properties of Enkephalin Degrading Enzyme (NEP and APN) Inhibitor Prodrugs," J. Med. Chem., vol. 44, May 21, 2001, pp. 3523-3530.
Le Guen, S., et al., "Pain management by a new series of dual inhibitors of enkephalin degrading enzymes: long lasting antiniciceptive properties and potentiation by CCK2 antagonist or methadone," International Association for the Study of Pain, Pain 104, Sep. 24, 2002, pp. 139-148.
Willis, W., et al., "Corneal Complications of Topical Anesthetic Abuse," Can. J. Ophthal, vol. 5, 1970, pp. 239-243.
Burstein, N., et al., "Electrophysiologic and morphologic effects of ophthalmic preparations on rabbit cornea epithelium," Invest. Ophthalmol. Vis. Sci., vol. 16, No. 10, Oct. 1977, pp. 899-911.
Rocha, G., et al., "Severe toxic keratopathy secondary to topical anesthetic abuse," Can. J. Opthalmol., vol. 30, No. 4, 1995, pp. 198-202.
Reiser, H., et al., "Letters to the Editor—Anethetic Abuse of the Cornea," Opthalmic Surgery, vol. 20, No. 1, Jan. 1989, pp. 72-73.

\* cited by examiner

AMINOPHOSPHINIC DERIVATIVES FOR PREVENTING AND TREATING EYE INFLAMMATION

CROSS-REFERENCE TO RELATED APPLICATIONS

This application is a National Phase Entry of International Patent Application No. PCT/FR2018/050545, filed on Mar. 9, 2018, which claims priority to French Patent Application Serial No. 1751912, filed on Mar. 9, 2017, and French Patent Application Serial No. 1759005, filed on Sep. 28, 2017, all of which are incorporated by reference herein.

BACKGROUND AND SUMMARY

The present invention relates to preventing and treating eye inflammation.

Inflammation or nerve lesions increase the local concentrations of enkephalins through various mechanisms, such as the migration of immune cells containing these endogenous opioid peptides to the site of the injury (Hassan et al., 1993, *Neuroscience*, 55, 185-195), the release of enkephalins by lymphocytes activated by inflammatory substances (chemokines, interleukins, LTB4, etc.) (Machelska, 2007, *Neuropeptides*, 41, 355-363), the release from inflamed keratinocytes (Gabrilovac et al., 2004, *Immunol. Lett.*, 91, 39-47) or instead from stimulated nerve fibres (Hassan et al., 1993, *Neuroscience*, 55, 185-195; Rittner et al., 2001, *Anesthesiology*, 95, 500-508). The regulation of opioid receptors also takes place in the ganglions of the dorsal root of the spinal cord, before these receptors are efficiently transported to the peripheral nerve endings (Hassan et al., 1993, *Neuroscience*, 55, 185-195).

Another family of inflammatory compounds, leukotrienes, are synthesised from arachidonic acid, the precursor of prostaglandins. They are very important agents in inflammatory response. The activation of LTB4 generates the migration of polynuclear neutrophil cells to the inflammation site but also the production of oxygenated free radicals and the expression of adhesion molecules. Prostaglandins and leukotrienes are thus mediators of different aspects of inflammation.

It has been shown that the use of opioids and particularly morphine could have a beneficial effect on eye inflammation. The effect of topical administration of morphine on the development of inflammation has been studied using a model for cauterising the corneal epithelium with silver nitrate in rats (Wenk et al., 2003, *Pain*, 105, 455-465). The use of morphine makes it possible to retard the development of an oedema of the stroma (12 h after treatment the treated corneas seem normal unlike the non-treated corneas) and the infiltration of immune cells (very few immune cells present).

The apparent increase in functional opioid receptors following a chemical aggression reinforces the hypothesis of the existence of an endogenous opioid system in the cornea activated by tissue lesion or inflammation. This effect is probably both analgesic (anti-hyperalgesic) and anti-inflammatory. The activation of an endogenous opioid system implies an enhanced availability of receptors and endogenous ligands.

Enkephalins (Met-enkephalin and Leu-enkephalin) are pentapeptides, endogenous opioids, initially isolated in the brain of mammals (Hugues et al., 1975, *Nature*, 258, 577-580). They are mainly bound to two classes of receptors, the mu and delta opioid receptors (Lord et al., 1977, *Nature*, 267, 495-499) the functions and localisations of which are different (Waksman et al., 1986, *Proc. Natl. Acad. Sci.*, 83, 1523-1527). On the other hand, it is known that enkephalins (Tyr-Gly-Gly-Phe-Met and Tyr-Gly-Gly-Phe-Leu) are physiologically inactivated by two zinc metallopeptidases, neprilysin (EC 3.4.24.11, NEP) which cleaves the $Gly^3$-$Phe^4$ bond (Malfroy et al., 1978, *Nature*, 276, 523-526) and aminopeptidase N (EC 3.4.11.2, APN) which cuts the $Tyr^1$-$Gly^2$ bond of these peptides. (Waksman et al., 1985, *Eur. J. Pharmacol.*, 117, 233-243; reviewed in Roques et al., 1993, *Pharmacol. Rev.*, 45, 87-146).

The aminophosphinic derivatives of the present invention, "true" mixed inhibitors of enkephalinases, that is to say jointly inhibiting APN and NEP, have been described in preceding patents and publications (WO98/18803; WO2010/010106; Chen et al., 2000, *J. Med. Chem.*, 43, 1398-1408; Chen et al., 2001, *J. Med. Chem.*, 44, 3523-3530; Le Guen et al., 2003, *Pain*, 104, 139-148; Bonnard et al., 2015, *Pharmacol. Res. Persp.*, 3(2), e00116, doi: 10.1002/prp2.116) as having analgesic activity. On the other hand, the use of these aminophosphinic derivatives as compounds making it possible to reduce, by topical administration, eye inflammation has never been described or suggested. It has also never been demonstrated that prodrugs of mixed inhibitors of NEP and APN could hydrolyse to give a compound capable of reaching its target at the level of the cornea and thereby enabling a response on the reduction of inflammation. In the same way, it has never been demonstrated that prodrugs of inhibitors of LTA4 hydrolase could hydrolyse to give a compound capable of reaching its target at the level of the cornea and thus enabling a response on the reduction of eye inflammation.

One of the aims of the present invention is thus to provide novel aminophosphinic type compounds capable of jointly inhibiting the two enzymatic activities (neprilysin and aminopeptidase N) responsible for the degradation of enkephalins, the latter being able to have an action within the context of eye inflammation. Yet, the Inventors have notably demonstrated that compound 1, the compound of the present invention, which is a prodrug of an inhibitor of LTA4 hydrolase (Tholander et al., 2008, *Chem. Biol.*, 15, 920-929) thereby preventing the formation of LTB4 (Bonnard et al., 2016, *Pharma. Res. Per.*, 3(2), 2015, e00116, doi: 10.1002/prp2.116), generates, by its topical administration, a compound having an inflammatory action in the front part of the eye.

Thus, the invention more specifically relates to compounds having formula (I), or a pharmaceutically acceptable salt of said compounds for the use thereof in treating and/or preventing eye inflammation:

$$R_1-NH-CH(R_2)-P(=O)(OH)-CH_2-C(R_3)(R_4)-CONH-C(R_5)(R_6)-COOR_7 \quad \text{(I)}$$

In which:

$R_1$ represents
  a hydrogen
  an (acyloxy)alkyl carbamate —C(=O)—O—C(R)(R')—OC(=O)—R" group in which R and R' represent, independently of each other, a hydrogen, an alkyl group and R" represents an alkyl group, $R_2$ represents:
  a hydrocarbon chain, saturated or unsaturated, linear or branched comprising 1 to 6 carbon atoms, $R_3$ and $R_4$ represent independently of each other:
- a hydrogen
- a phenyl or benzyl group, optionally substituted on the phenyl ring by:
  - 1 to 5 halogen atoms notably fluorine or bromine
  - a OH, SH, OR" or SR", R" radical having the same definition as previously
  - an amino group optionally mono- or di-substituted by an aliphatic group, cyclic or linear, with 1 to 6 carbon atoms
  - a trifluoromethyl group
  - an aromatic or heteroaromatic group with 5 or 6 atoms
- a heteroaromatic group with 5 or 6 atoms, containing 1 or 2 heteroatom(s) taken from oxygen, nitrogen or sulphur, the sulphur and nitrogen atoms being able to be oxidised in S-oxide or N-oxide form
- a methylene substituted by a heterocycle with 5 or 6 atoms, aromatic or saturated, the heteroatom being oxygen, nitrogen or sulphur, the nitrogen and sulphur atoms being able to being oxidised in N-oxide or S-oxide form $R_3$ and $R_4$ do not represent simultaneously a hydrogen atom,
$R_5$ and $R_6$ represent independently of each other
- a hydrogen atom
- a hydrocarbon chain, saturated or unsaturated, linear or branched with 1 to 6 carbon atoms, $R_7$ represents
- a hydrogen
- a $CH_2COOR'''$ or $CH(CH_3)COOR'''$ radical, $R'''$ representing:
  - a saturated hydrocarbon chain with 1 to 6 carbon atoms, optionally substituted by a $C_1$ to $C_3$ alkoxy group,
  - a C to C cycloalkyl group
  - a phenyl, benzyl, heteroaromatic or heteroaromatic alkyl group
- a $CH(R)O-C(O)OR'$ or $CH(R)OC(O)R'$ group in which R and R' have the same definitions as previously.

Eye inflammation may notably be due to a traumatism, an infection and/or an auto-immune disease. The compounds according to the invention are advantageously used to improve the process of eye healing and/or cicatrisation, and thus prevent for example the onset of a toxic keratopathy, problems at the level of the epithelium or permanent scars. The compounds according to the invention may notably be used for preventing or treating inflammation of the cornea, the sclera, the uvea. Thus, the compounds according to the invention are advantageously used for preventing or treating eye inflammation linked to keratitis, scleritis, episcleritis, uveitis, a cataract, a synechia, a macular oedema, a detachment of the retina, an ocular hypertension and degeneration of the optic nerve caused by glaucoma. In particular, the compounds according to the invention are also used to prevent the formation of new vessels (neovascularisation).

The present invention also relates to an ophthalmic composition including a compound of formula (I) of the invention, in particular eye lotion, ophthalmic ointment, ophthalmic gel, or ophthalmic insert, notably for the use thereof in treating and/or preventing eye inflammation. In the present invention, the patient suffering from eye inflammation is typically an animal, preferably an animal, advantageously it is a human.

Eye Inflammation

Inflammation is a physiological response of the organism to an aggression which may be of various origins: traumatism; infection; auto-immune disease. At the level of the eye, inflammation notably causes a rupture of the barriers that isolate the eye from the general circulation, enabling the entry of proteins and cells which participate in the inflammatory process and have an impact on cicatrisation.

Numerous topical ophthalmic anaesthetics slow down the healing process, which can lead to complications such as a toxic keratopathy, problems at the level of the epithelium or permanent scars (Willis and Laibson, 1970, *Can. J. Ophthalmol.*, 5, 239-243; Burstein and Klyce, 1977, *Invest. Ophthalmol. Vis. Sci.*, 16 (10), 899-911; Rocha et al., 1995, *Can. J. Ophthalmol.*, 30(4), 198-202). Consequently, physicians often hesitate to prescribe topical anaesthetics, even for serious eye pain (Reiser and Laibson, 1989, *Ophthalmic Surg.*, 20, 72-73).

Inflammation can affect the cornea and the sclera on the surface of the eye; the uvea composed of the iris, the ciliary body and the choroid; and at the origin of the optic nerve, the retina and the papilla. Advantageously, eye inflammation affects the sclera on the surface of the eye; the uvea composed of the iris, the ciliary body and the choroid; and at the origin of the optic nerve, the retina and the papilla. This eye inflammation may be responsible for opacity and lesions of the cornea (keratitis); lesions of the sclera (scleritis and episcleritis); uveitis with for complication an opacification of the crystalline lens (cataract); adherence of the iris to the crystalline lens (synechiae); a macular oedema; a detachment of the retina; an ocular hypertension and degeneration of the optic nerve caused by glaucoma; the formation of new vessels (neovascularisation); etc. In one particular embodiment, the eye inflammation is not necessarily caused by a keratitis.

Compounds According to the Invention:

In the present invention, "pharmaceutically acceptable" is taken to mean that which is useful in the preparation of a pharmaceutical composition which is generally safe, non-toxic and neither biologically or otherwise undesirable and which is acceptable for both veterinary use and for human pharmaceutics. "Pharmaceutically acceptable salts" of a compound is taken to mean in the present invention salts that are pharmaceutically acceptable, as defined herein, and which have the desired pharmacological activity of the parent compound. Within the scope of the present invention, they are addition salts obtained with a mineral or organic base. Thus, the salt formed corresponds:
- either to the replacement of an acid proton by a metal ion, for example an alkali metal ion ($Na^+$, $K^+$ or $Li^+$ for example), an alkaline-earth metal ion (such as $Ca^{2+}$ or $Mg^{2+}$) or an aluminium ion,
- or to the coordination of this acid proton with an organic or inorganic base.

Acceptable organic bases include amines such as ammonia, diethanolamine, ethanolamine, N-methylglucamine, triethanolamine, triethylamine, tromethamine and similar. Acceptable inorganic bases include aluminium hydroxide, calcium hydroxide, lithium hydroxide, potassium hydroxide (caustic potash), sodium carbonate and sodium hydroxide (soda). Advantageously, the pharmaceutically acceptable salts of the compounds of the invention will be addition salts obtained with a pharmaceutically acceptable mineral or organic base, such as lithium hydroxide, soda, potassium hydroxide, ammonia, a tertiary amine of formula $NR_aR_bR_c$, where $R_a$, $R_b$ and $R_c$ represent, independently of each other, an alkyl group such as defined below, such as triethylamine, or instead a basic amino acid such as lysine or arginine and derivatives thereof.

"Unsaturated" is taken to mean, in the sense of the present invention, that the hydrocarbon chain includes one or more unsaturation(s). "Unsaturation" is taken to mean, in the sense of the present invention, a double or triple bond.

"Halogen atom" is taken to mean, in the sense of the present invention, a fluorine, chlorine, bromine or iodine atom. Advantageously, it is a fluorine, bromine or chlorine atom. More advantageously, it is a fluorine or bromine atom, and preferably fluorine.

"Amino" group is taken to mean, in the sense of the present invention, a group of formula —NR*R**, where R* and R** represent, independently of each other, a hydrogen atom or a hydrocarbon group, saturated or unsaturated, linear, branched or cyclic, comprising 1 to 6, preferably 1 to 4, carbon atoms, or R* and R** together form, with the nitrogen atom that bears them, a 5 or 6 membered heterocycle, saturated or not, and not comprising other heteroatoms than the nitrogen which bears the two R* and R** radicals. In particular, the amino group may be a —$NH_2$, —NHMe, —NHEt, —NHPr, NHiPr, —NHBu, —NHiBu, —NHtBu, piperidinyl or pyrrolidinyl group.

"Aromatic" group is taken to mean, in the sense of the present invention, an aromatic group, preferably comprising 5 to 10 carbon atoms, unless stated otherwise, and including one or more fused rings, such as for example a phenyl or naphthyl group. Advantageously, it is phenyl.

"Heteroaromatic" group is taken to mean, in the sense of the present invention, any aromatic group as defined above in which one or more carbon atom(s) has(have) been replaced by one or more heteroatom(s), advantageously 1 to 4 and, even more advantageously 1 to 2, such as for example sulphur, nitrogen or oxygen atoms, the sulphur and nitrogen atoms optionally being able to be in S-oxide or N-oxide form. Examples of heteroaromatic groups are the furyl, thienyl, pyrrolyl, pyridinyl, pyrimidyl, pyrazolyl, imidazolyl, tetrazolyl or indanyl groups.

"Heteroaromatic ring with 5 or 6 atoms" is taken to mean, in the sense of the present invention, a heteroaromatic group such as defined above only comprising a Clean Specification single ring with 5 or 6 atoms. It is notably a thienyl, pyrrolyl, pyridinyl, pyrimidyl, pyrazolyl, imidazolyl or tetrazolyl group.

"Heterocycle" is taken to mean, in the sense of the present invention, a hydrocarbon ring, advantageously with 5 or 6 atoms, of which one or more carbon atom(s) have been replaced by one or more heteroatom(s), advantageously 1 to 4 and, even more advantageously 1 to 2, such as for example sulphur, nitrogen or oxygen atoms, the sulphur and nitrogen atoms optionally being able to be oxidised in N-oxide and S-oxide form. Unless stated otherwise, this ring could be saturated or aromatic. In the case where the heteroatom(s) is (are) selected from nitrogen and sulphur, the heterocycle may be in particular a: piperidinyl, pyrrolidinyl, pyrrolyl, thienyl, pyrrazolyl, imidazolyl, pyridinyl, pyridazinyl, pyrimidinyl, piperazinyl, thiadiazolyl, tetrahydrothienyl or thiazolyl group.

"Alkyl" is taken to mean, in the sense of the present invention, a saturated hydrocarbon chain, linear or branched, comprising 1 to 6 carbon atoms, unless stated otherwise. It is in particular the methyl, ethyl, n-propyl, isopropyl, n-butyl, iso-butyl, sec-butyl, tert-butyl, n-pentyl, n-hexyl group.

"Cycloalkyl" is taken to mean, in the sense of the present invention, a saturated hydrocarbon ring comprising 5 to 8 carbon atoms, in particular the cyclohexyl, cyclopentyl or cycloheptyl group.

"Heteroaromatic alkyl" is taken to mean, in the sense of the present invention, a heteroaromatic group as defined above bound to the molecule via an alkyl group such as defined above. It is in particular a thienylmethyl or furylmethyl group.

In a first alternative, $R_1$ represents an (acyloxy)alkyl carbamate —C(=O)—O—C(R)(R')—OC(=O)—R'' group. In particular, $R_1$ represents a —C(=O)—O—CHMe-OC(=O)—$CHMe_2$ group. In a second alternative, $R_1$ represents a hydrogen atom. Also advantageously, the radical $R_2$ represents a saturated hydrocarbon chain, linear or branched, comprising 1 to 4 carbon atoms. Preferably, the radical $R_2$ represents a methyl group.

According to an advantageous alternative of the invention, $R_3$ represents a hydrogen atom and $R_4$ is as defined previously. Advantageously, $R_3$ represents a hydrogen atom and $R_4$ represents a benzyl group optionally substituted by 1 to 5 halogen atom(s) such as fluorine or bromine, a phenyl or a 5 or 6 membered heteroaromatic group, preferably $R_4$ represents a benzyl group optionally substituted by a phenyl (notably in para position). In particular, $R_3$ represents a hydrogen atom and $R_4$ represents a benzyl group substituted, in para position, by a halogen atom, such as a bromine atom, or by a phenyl. Also advantageously, the $R_4$ radical represents a benzyl group optionally substituted by 1 to 5 halogen atom(s) such as fluorine or bromine, a phenyl or a 5 or 6 membered heteroaromatic group, preferably $R_4$ represents a benzyl group optionally substituted by a phenyl (notably in para position).

Also advantageously, the $R_5$ radical represents a hydrogen atom. Also advantageously, the $R_6$ radical represents an alkyl group such as a methyl group. Also advantageously, the $R_7$ radical represents a hydrogen atom or a benzyl.

According to an advantageous alternative of the invention, the radicals have the following signification:
$R_1$ represents a —C(=O)—O—C(R)(R')—OC(=O)—R'' group in which R represents a hydrogen atom and R' and R'' represent an alkyl group;
$R_2$ represents an alkyl group,
$R_3$ represents a hydrogen atom;
$R_4$ represents a benzyl group substituted in para position by a halogen atom (bromine) or by a phenyl;
$R_5$ represents a hydrogen atom;
$R_6$ represents an alkyl group;
$R_7$ represents a hydrogen atom.

According to a particular embodiment, the compound of the invention is selected from the following compounds:
Benzylic ester of 2-(2-biphenyl-4-ylmethyl-3-{hydroxy-[1-(1-isobutyryloxy-ethoxycarbonylamino)-ethyl]-phosphinoyl}-propionylamino)-propionic acid
2-(2-Biphenyl-4-ylmethyl-3-{hydroxy-[1-(1-isobutyryloxy-ethoxycarbonylamino)-ethyl]-phosphinoyl}-propionylamino)-propionic acid
Ethyl ester of 2-(2-biphenyl-4-ylmethyl-3-{hydroxy-[1-(1-isobutyryloxy-ethoxycarbonylamino)-ethyl]-phosphinoyl}-propionylamino)-propionic acid
Ethoxycarbonyloxy ester of 2-(2-biphenyl-4-ylmethyl-3-{hydroxy-[1-(1-isobutyryloxy-ethoxycarbonylamino)-ethyl]-phosphinoyl}-propionylamino)-propionic acid
Benzylic ester of 2-(2-(4-bromo-benzyl)-3-{hydroxy-[1-(1-isobutyryloxy-ethoxycarbonylamino)-ethyl]-phosphinoyl}-propionylamino)-propionic acid
2-(2-(4-Bromo-benzyl)-3-{hydroxy-[1-(1-isobutyryloxy-ethoxycarbonylamino)-ethyl]-phosphinoyl}-propionylamino)-propionic acid
Benzylic ester of 2-(2-biphenyl-4-ylmethyl-3-{hydroxy-[1-(amino)-ethyl]-phosphinoyl}-propionylamino)-propionic acid
2-(2-Biphenyl-4-ylmethyl-3-{hydroxy-[1-(amino)-ethyl]-phosphinoyl}-propionylamino)-propionic acid Ethyl ester of 2-(2-biphenyl-4-ylmethyl-3-{hydroxy-[1-(1amino)-ethyl]-phosphinoyl}-propionylamino)-propionic acid Ethoxycarbonyloxy ester of 2-(2-biphenyl-4-ylmethyl-3-{hydroxy-[1-(amino)-ethyl]-phosphinoyl}-propionylamino)-propionic acid

Benzylic ester of 2-(2-(4-bromo-benzyl)-3-{hydroxy-[1-(amino)-ethyl]-phosphinoyl}-propionylamino)-propionic acid 2-(2-(4-Bromo-benzyl)-3-{hydroxy-[1-(amino)-ethyl]-phosphinoyl}-propionylamino)-propionic acid Ethyl ester of 2-(2-(4-bromo-benzyl)-3-{hydroxy-[1-(amino)-ethyl]-phosphinoyl}-propionylamino)-propionic acid.

Preferably, it is compound 1:

Compound 1

The compounds of formula (I) have been described as double inhibitors of APN and NEP and have analgesic activities in numerous central or peripheral pain models after intravenous or oral administration (Chen et al., 2000, *J. Med. Chem.*, 43, 1398-1408; Bonnard et al., 2015, *Pharmacol. Res. Persp.*, 3(2), e00116, doi: 10.1002/prp2.116). The compounds of formula (I) may be synthesised, for example, by the methods described in: FR 2 755 135 and FR 2 934 267. Compound 1, for example, may be synthesised as described in Chen et al., 2000, *J. Med. Chem.*, 43, 1398-1408. The compounds of formula (I) are formulated in accordance with methods described by those skilled in the art, in particular for the desired administration route. In particular, the compounds are formulated in the form of an ophthalmic composition, in particular eye lotions, ophthalmic ointments, ophthalmic gels, or ophthalmic inserts.

Preferentially, the administered compositions of the present invention will be formulated as solutions, suspensions or other mixtures for topical administration, in Clean Specification particular ocular administration. Consequently, such compositions are formulated so as to respect: good tolerance (in particular acceptable pH), physiological osmolarity. It is moreover preferable that the compositions are sterile and formulated in such a way as to avoid bacterial contamination during use. The ophthalmic solutions are advantageously limpid, characterised by an absence of particles. The suspensions are advantageously characterised by a particle size below 25 μm. As regards pharmaceutical formulations for ocular administration, the following may notably be cited:

Eye lotions: in the form of sterile solutions, suspensions, emulsions, containing one or more active ingredients. Aqueous or water soluble solvents or mixtures of solvents are preferred. The eye lotions may be packaged in multi-dose or single-dose packaging.

Ophthalmic ointments, that is to say semi-solid preparations, sterile, intended to be applied on the conjunctiva, containing one or more active ingredients and appropriate excipients (Vaseline, liquid paraffin).

Ophthalmic gels, that is to say semi-solid preparations, sterile, intended to be applied on the conjunctiva, containing one or more active ingredients and appropriate excipients. The excipient is advantageously a hydrophilic polymer that gels in the presence of water (carbomer, Carbopol®, polyacrylic acid).

Ophthalmic inserts, that is to say solid or semi-solid preparations, sterile, intended to be inserted in the conjunctival sac. They are in general constituted of a reservoir of active ingredient embedded in a matrix surrounded by a membrane making it possible to control release. The active ingredient is released progressively.

Aqueous solutions will preferably be used because they are more easily formulated, and it is also easier for a patient to self-administer such a composition by means of an instillation of 1 or 2 drops of the solution in the affected eye. After all, the composition could also be a suspension, a viscous or semi-viscous gel or other types of solid or semi-solid compositions.

The vehicle used preferably for the ophthalmic formulations of the present invention is Milli-Q water, and preferentially a physiological saline solution. In order to avoid any pH drift during storage, the pH of such a solution will preferably be maintained between 5.0 and 8, notably between 5.5 and 8.0, and preferentially between 6.5 and 7.2, with an appropriate buffer such as acetate, citrate, phosphate or borate buffers. The formulations could also contain conventional, pharmaceutically acceptable, preservatives, stabilisers and/or compounds favouring penetration. Thus, the ophthalmic composition is advantageously an aqueous solution, having advantageously a pH ranging from 5.0 to 8, notably between 5.5 and 8.0.

The compositions administered in accordance with the methods described in the present invention contain an active quantity for ophthalmic use of a compound of formula (I). This signifies a sufficient quantity to prevent or relieve eye inflammation. Generally, the compositions described in the present invention will contain between 0.01% and 3% (weight/volume) of a compound of formula (I). Preferably, the compositions of the present invention will contain between 0.1 and 1% (weight/volume) of a compound of formula (I). Thus, the ophthalmic composition advantageously includes 0.01% to 3% in weight by volume of said compound of formula (I), more advantageously 0.1% to 1% in weight by volume. The administered composition could also contain other varied ingredients such as, but not in an exhaustive manner, surfactants, agents that influence osmolarity, buffers, preservatives, co-solvents or viscosifying agents.

Different compounds influencing osmolarity may be used to adjust the osmolarity of a solution in order to be close to the composition of natural tears. For example, sodium chloride, potassium chloride, magnesium chloride, calcium chloride, dextrose and/or mannitol may be used in order to be close to physiological osmolarity (generally of the order of 150-450 mOsm and preferentially 250-350 mOsm). The preservatives that may be used in the ophthalmic formulations of the present invention may be, but are not limited to, benzalkonium chloride, chlorobutanol, benzododecinium bromide, methyl parabene, propyl parabene, thimerosal, phenylmercuric acetate and phenylmercuric nitrate. Such preservatives are generally used at a dose of 0.001 to 1.0% weight/volume.

Agents acting on the viscosity that may be used in the ophthalmic formulations of the present invention may be, but are not limited to, monomeric polyols, povidone, hydroxypropylmethyl cellulose, poloxamers, carboxymethyl cellulose, carbomers or hydroxyethylcellulose, dextrans such as dextran 70, water soluble proteins such as gelatine, etc. The agents acting on penetration that may be used are for example, organic solvents such as dimethylsulphoxide or other sulphoxides, dimethylacetamide and pyrrolidones; certain amide compounds of heterocyclic amines, glycols (e.g. propylene glycol); propylene carbonates; oleic acid; alkylated amines and other ammonium salt derivatives; various anionic, cationic or non-ionic surface active agents, etc. In one preferred embodiment, a formulation of the present invention includes a cyclodextrin, such as hydroxypropyl beta-cyclodextrin or instead sulphobutyl ether beta-cyclodextrin, or sodium polystyrene sulphonate. Thus, the ophthalmic composition advantageously further includes a cyclodextrin, such as hydroxypropyl beta-cyclodextrin or instead sulphobutyl ether beta-cyclodextrin, or sodium polystyrene sulphonate.

BRIEF DESCRIPTION OF THE DRAWINGS

FIGS. 1 and 2 serve as inflammatory control for FIGS. 4 and 5. FIG. 3 serves as inflammatory control for FIGS. 6 and 7.

EXAMPLES

Example 1: Pharmacological Activity of Compound 1 (See Structure Above) in an Inflammatory Model Induced by Lipopolysaccharide (LPS, 50 µg)

A corneal epithelial lesion (abrasion designated "scratch" in the figures) is made on the right eye of male mice C57Bl/6, 8 weeks old, using a trephine (diameter 1.5 mm) on the anaesthetised animal (isoflurane). A drop (10 µl) of LPS (50 µg) is Clean Specification deposited on the injured area and is left in contact with the cornea until the animal awakens. The experimentalist ensures the animal awakens correctly, which occurs within two minutes following the intervention.

The first topical treatment using a solution of PBS (phosphate buffer pH=7.4) (1×) or a solution of compound 1 (10 mM of compound 1 in a solution of PBS (1×)) was carried out 2 h after the instillation of LPS. This treatment was extended 2 times a day for 5 days. Four animal cages were studied:

Cage 1: Scratch LPS (instillation J1)+PBS 1× (n=5)
Cage 2: Scratch LPS (2×) (instillations J1 and J4)+PBS 1× (n=5)
Cage 3: Scratch LPS (instillation J1)+compound 1 (10 mM) (n=5)
Cage 4: Scratch LPS (2×) (instillations J1 and J4)+compound 1 (10 mM) (n=5)

The eye inflammation of the mice was evaluated on the $5^{th}$ day using a confocal microscope in vivo. This enable images to be obtained (cellular and intercellular definition) of the cornea including the corneal epithelium, the nerve plexus, the stroma and the endothelium thanks to a capsule (Tomocap)/corneal module of the apparatus placed in contact with the cornea. The morphological changes of all the cells constituting the cornea and the corneal nerves are easily observable and quantifiable. All of the animals were anaesthetised by intraperitoneal injection (ketamine 100 mg/kg and xylazine 10 mg/kg). Lubrithal® gel was deposited on the untreated eye.

Figure 1:
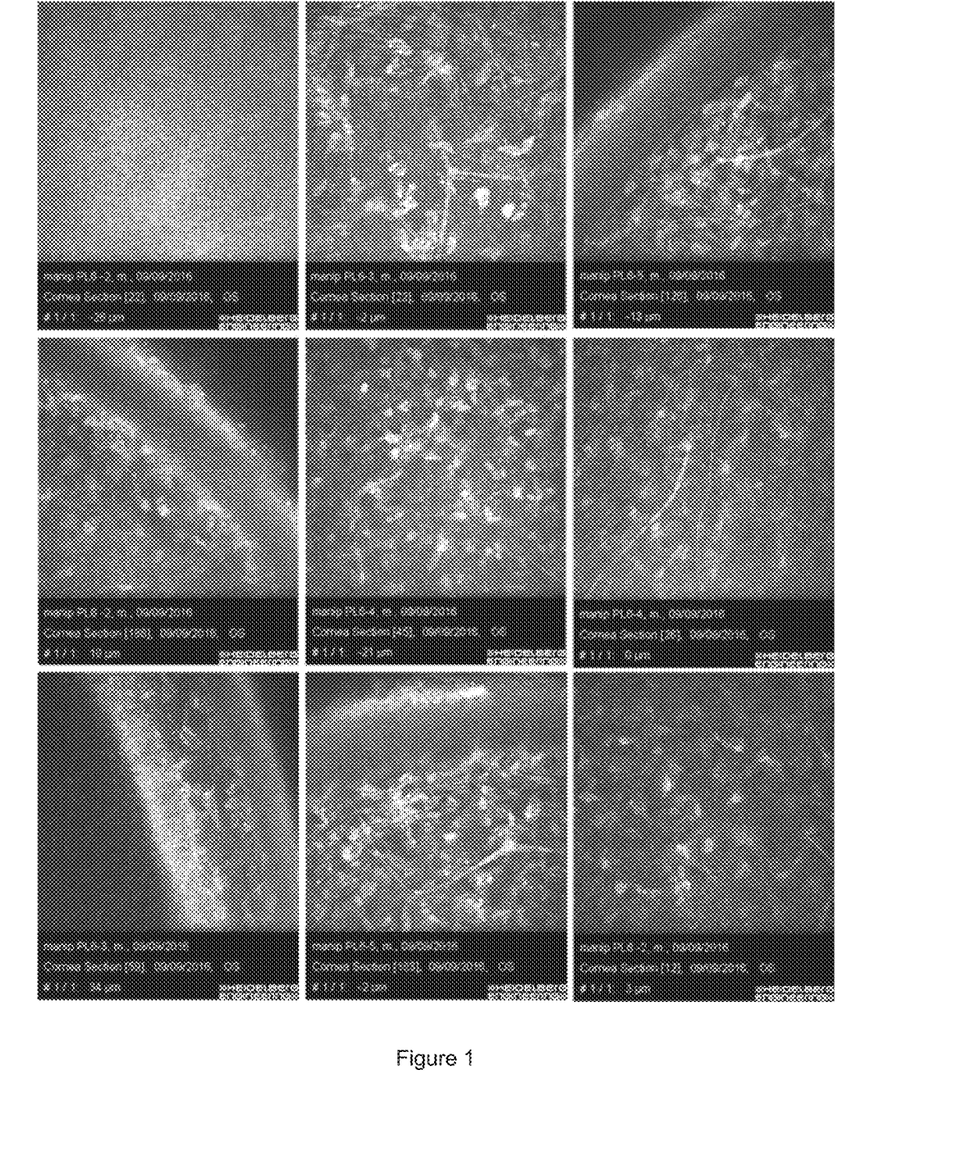
FIG. 1 shows images of the different control mouse corneal sections Cage 1: scratch+LPS+PBS.
Figure 2:
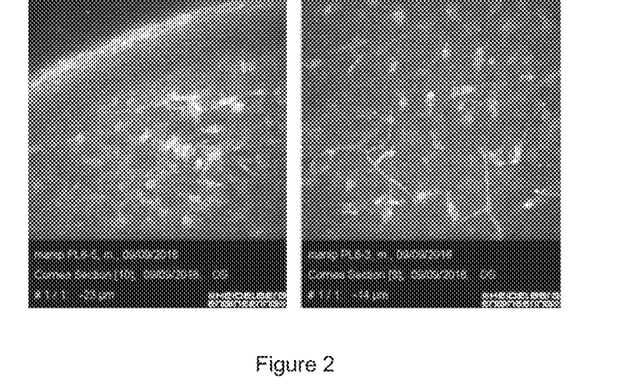
FIG. 2 shows images of the different control mouse corneal sections Cage 1: scratch+LPS+PBS.
Figure 3:
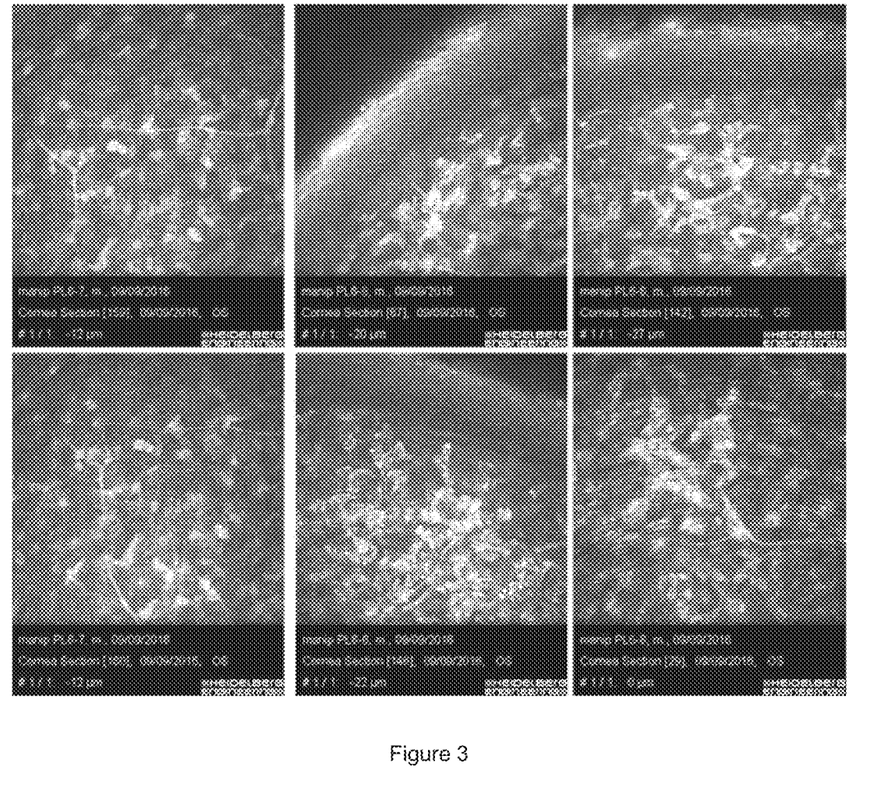
FIG. 3 shows images of the different control mouse corneal sections Cage 2: scratch+LPS (2×)+PBS.
Figure 4:
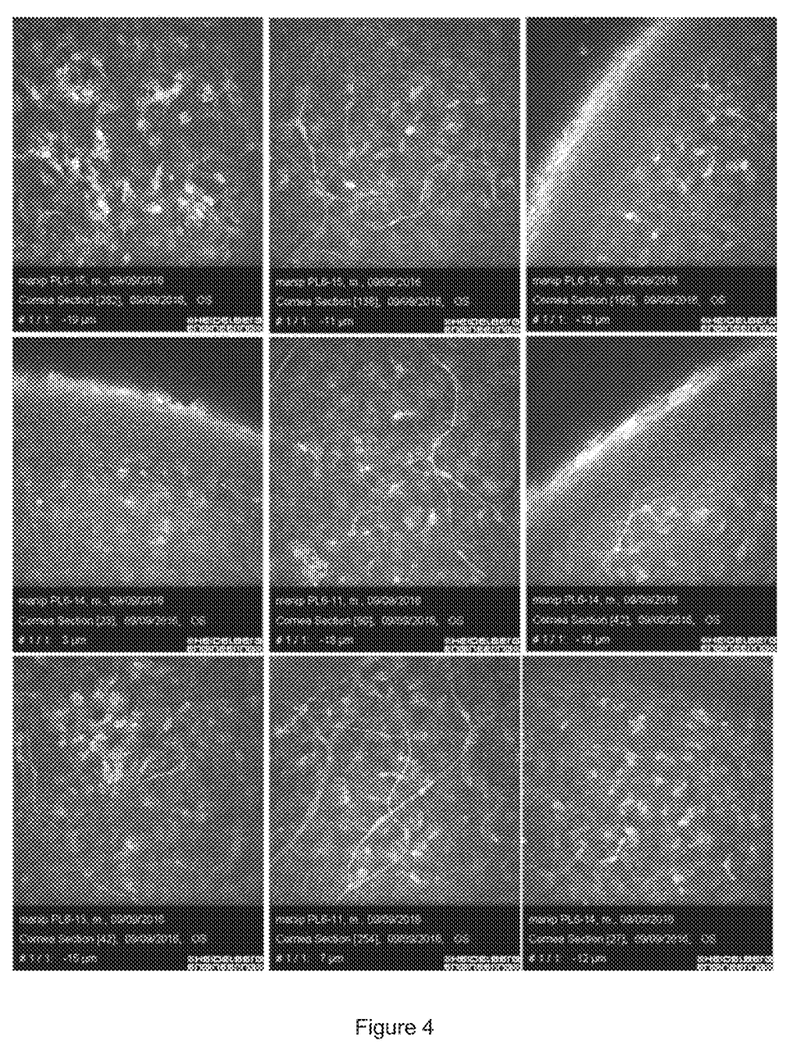
FIG. 4 shows images of the different treated mouse corneal sections Cage 3: scratch+LPS (1×)+Compound 1 (10 mM).
Figure 5:
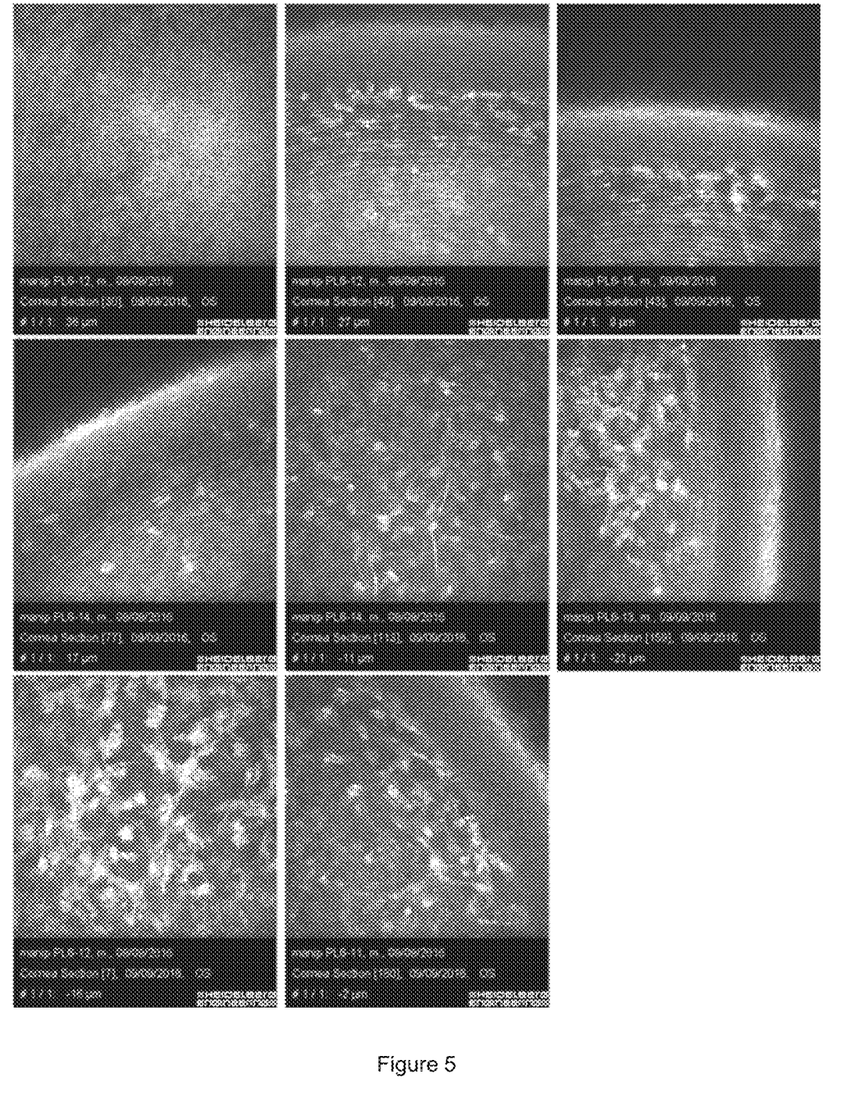
FIG. 5 shows images of the different treated mouse corneal sections Cage 3: scratch+LPS (1×)+Compound 1 (10 mM).
Figure 6:
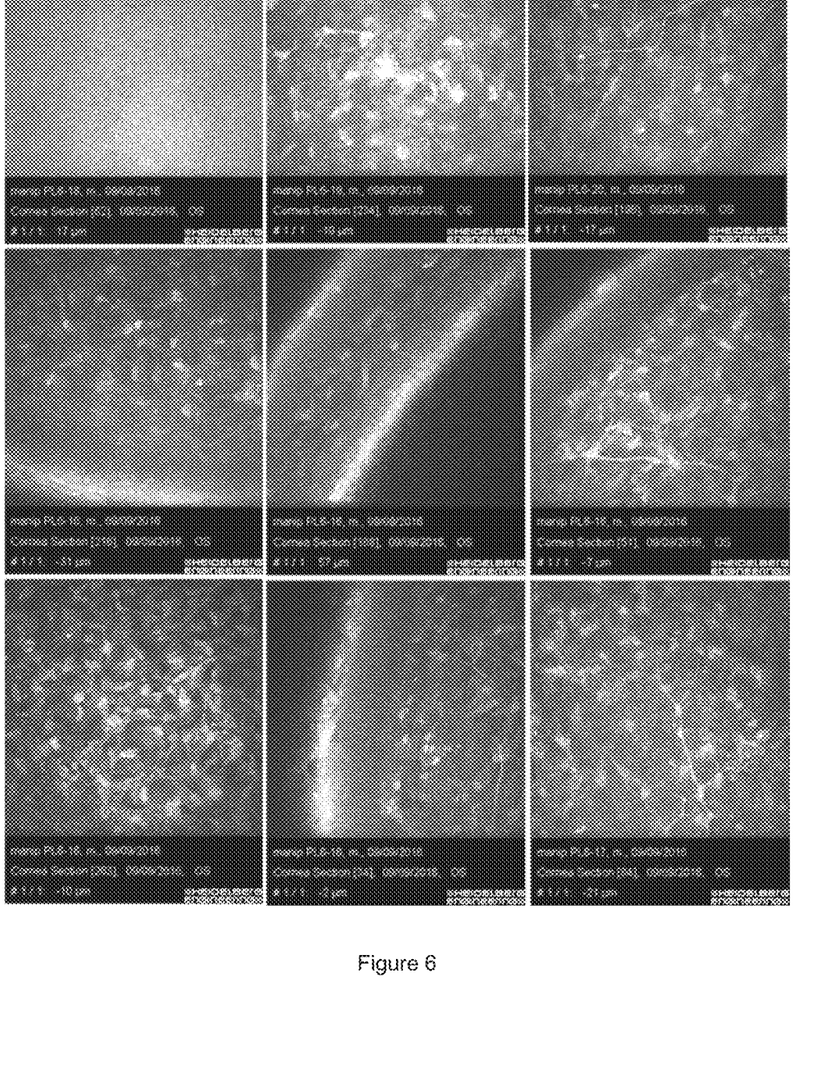
FIG. 6 shows images of the different treated mouse corneal sections Cage 4: scratch+LPS (2×)+Compound 1 (10 mM).
Figure 7:
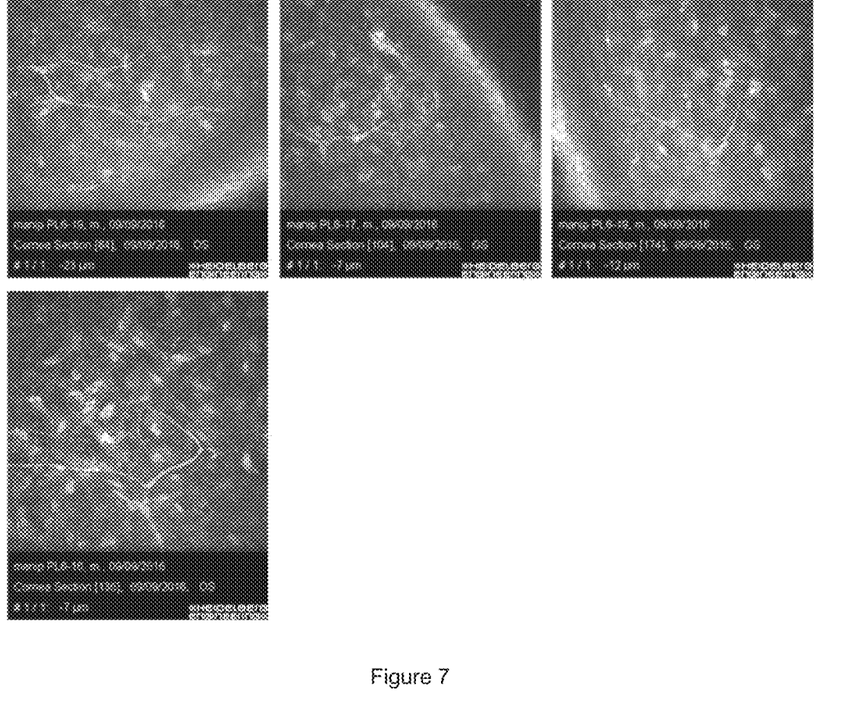
FIG. 7 shows images of the different treated mouse corneal sections Cage 4: scratch+LPS (2×)+Compound 1 (10 mM).
Figure 8:
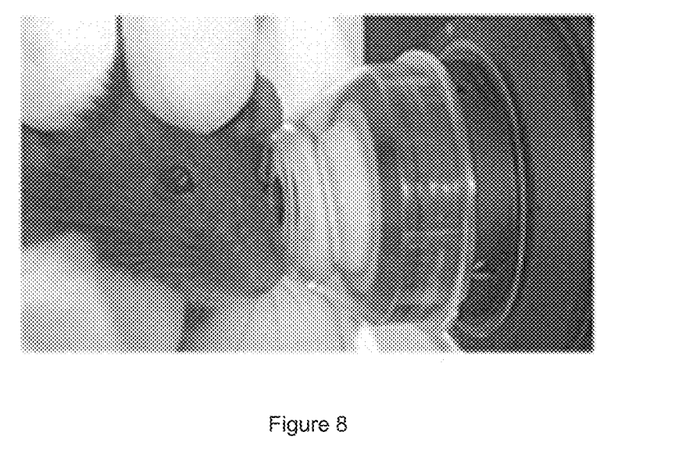
FIG. 8 shows a photograph of the experimental set-up for imaging the eye surface (Tomocap capsule) used in the examples below.

The experimental set-up used in this procedure is identical to that used routinely in human clinical use. The animals are anaesthetised and both eyes receive Lubrithal® gel. The experimental set-up is situated in a room dedicated to imaging of the eye surface. This method is non-invasive. The complete examinations take 5 minutes at the most per animal (see FIG. 8). In the images obtained for the different groups, represented in FIGS. 1 to 7, it may be seen that the corneas of animals having received a twice-daily instillation of compound 1 (10 mM) for 5 consecutive days are less inflammatory compared to those of animals having received PBS 1×.

Example 2

The objective of this example is to demonstrate the anti-inflammatory effect of compounds of formula (I) as defined above and in claim 1, and more specifically compound 1, two markers linked to this inflammatory state: ATF3 and Iba1 (as described by Launay et al. in Neurobiol. Dis., 88 (2016), 16-28) were quantified, in the trigeminal ganglion, by immuno-histology, in the inflammatory keratitis model induced by LPS in mice as described in example 1. ATF3 (activating transcription factor 3) is a transcription factor of the family of ATF which modulates the inflammatory response of several diseases. In physiological conditions, the primary sensory neurones express very little ATF3. An increase in the number of positive neurones for ATF-3 then underlines neuronal suffering linked to an inflammatory process. In the same way, Iba1 (ionized calcium-binding adapter molecule 1) is expressed in the microglial cells activated by the presence of macrophages and thus by an inflammatory process.

1. Immuno-Histological Studies
Tissue Preparation
Two hours after the final instillation of LPS, a mixture of 300 µL of ketamine 1000 U (100 mg/kg of body weight) and xylazine (10 mg/kg of body weight, Virbac, France) was injected by intraperitoneal route to deeply anaesthetise the animals. After fixation, the trigeminal ganglia and the eyes were carefully dissected and post-fixated for 48 h in the same fixation mixture. Sections (40 µm) of the complex of the trigeminal sub-nucleus (trigeminal nucleus, TG) were formed using a Vibratom (Leica Microsystems, Germany). The TG were placed in a 10% solution of sucrose in 1×PBS (overnight), then in a 30% solution of sucrose before freezing at −20° C. in a mixture of 7.5% gelatine and 10% sucrose. Sections (14 µm) were made in the cryostat for the TG and the eyes and conserved at −20° C.

Marking by Immunofluorescence
After three washings in 1×PBS, the TG sections were placed in a fixation solution containing 3% of normal horse serum and 0.1% of triton X-100 for 2 h, then incubated with a primary antibody at 4° C. for 48 h. The antibodies used in this study are rabbit anti-ATF3 (Sigma-Aldrich: HPA001562, 1/500) and anti-goat Iba1 (Abcam: ab5076, 1/500). ATF3 was amplified using horse biotin combined with a rabbit antibody (1/500; Vector Laboratories) for 1 h and finally revealed by incubation with streptavidin-Alexa Fluorine 488/555 (1/500; Invitrogen). Iba1 was revealed using donkey streptavidin Alexa Fluorine 594 combined with anti-goat (1/500; Invitrogen) for 1 h.

The TG sections were treated using avidin-biotin peroxidase (Vectastain ABC Kit, Vector Laboratories) for ATF3 and Iba1 immuno-reactivity. The TG sections were incubated with a 3% solution of $H_2O_2$ for 20 min. They were rinsed three times with 1×PBS then incubated with 3% NHS for 2 h at room temperature before incubation with the primary antibodies overnight at 4° C. The sections were rinsed three times with 1×PBS, incubated for 1 h at room temperature with biotinylated secondary anti-rabbit IgG (1/500; Vector). The sections were rinsed three times in 1×PBS, incubated in a solution containing the complex Avidin Biotin Peroxidase (Elite, Vector) for 1 h, then rinsed three times with 1×PBS.

2. Microscopy and Quantification of the Immunohistochemical Labelling
Microscopic Apparatus
The cells and the tissue sections were examined either with a Zeiss M1 epifluorescence microscope or with an Olympus FV1000 confocal laser scanning microscope. The epifluorescence microscope (Axio Imager M1; Carl Zeiss) was equipped with a digital camera (Axio Cam HRC, Carl Zeiss) and image acquisition software (Zen; Carl Zeiss). The confocal microscope (Olympus FV1000) was equipped with an argon ion laser (488 nm) and laser diodes (405 and 559 nm). The images were acquired sequentially to reduce problems of excitation and emission crosstalk. The size was defined according to the Nyquist-Shannon sampling theorem (1024*1024 pixels). The objectives used were Olympus PlanApo (10/0.40 NA) or PlanApoN (60/1.42 NA, oil immersion) objectives. The tissue sections were also scanned with the Nanozoomer 2.0-HT digital scanner (C9600, Hamamatsu Photonics), equipped with the 3-CCD TDI camera (Hamamatsu Photonics). TIFF images were thus obtained. The microscopes were calibrated with control groups.

Figure 9:
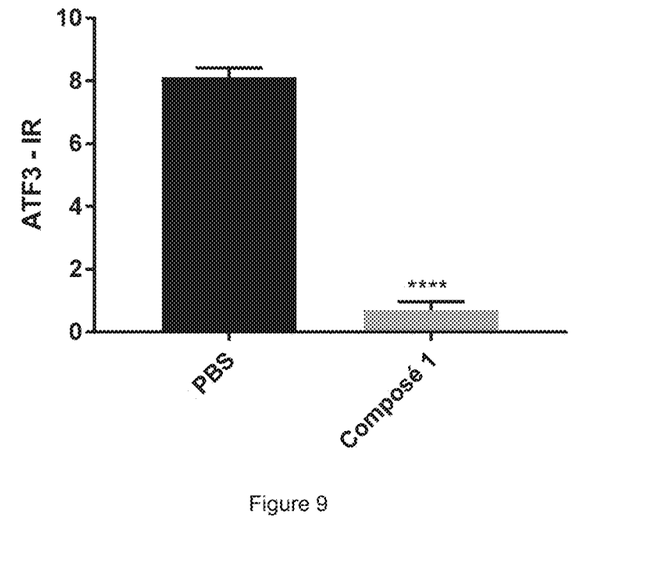
FIG. 9 shows an expression of the gene ATF3 (activating transcription factor 3) in the trigeminal ganglion. In an LPS inflammation model, the twice-daily treatment for 5 days by compound 1, versus the PBS control group, considerably reduces the expression of ATF3, neuronal stress marker linked to an inflammatory process.
Figure 10:
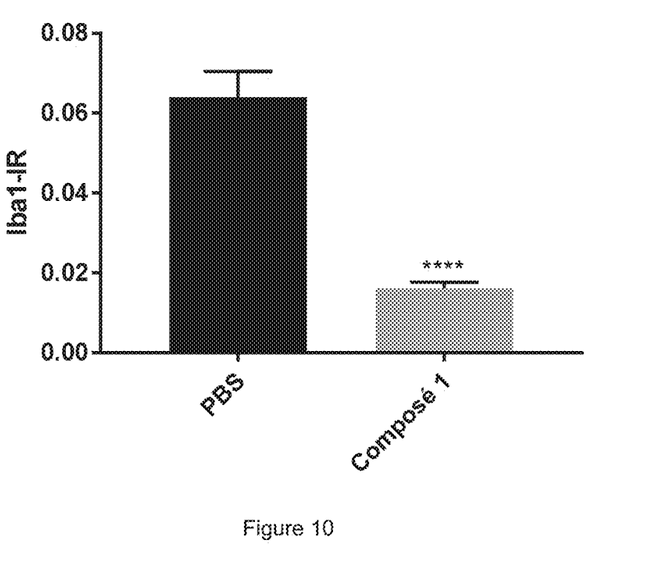
FIG. 10 shows a relative percentage of protein Iba1 (ionized calcium binding adaptor molecule 1) in the trigeminal ganglion. In an LPS inflammation model, the twice-daily treatment for 5 days by compound 1, versus the PBS control group, considerably reduces the coloration of activated microglial cells expressing Iba-1, sign of the production of macrophages.

3. Results
The results obtained are reported in FIGS. 9 and 10. It clearly appears that the twice-daily instillation of 10 mM, for 5 days by compound 1 (PL265), in an inflammatory keratitis model induced by LPS in mice makes it possible to reduce significantly the expression of ATF3 and Iba1 compared to an identical instillation with PBS and thus to demonstrate less extensive inflammation.

The invention claimed is:

1. A method for treating or preventing eye inflammation in a subject in need thereof, the method comprising administering a compound having formula (I) or a pharmaceutically acceptable salt of the compound to the subject, the compound of formula (I) comprising:

in which:

$R_1$ represents:
  a hydrogen, or
  an (acyloxy)alkyl carbamate —C(=O)—O—C(R)(R')—OC(=O)—R" group in which R and R' represent, independently of each other, a hydrogen, an alkyl group and R" represents an alkyl group;

$R_2$ represents:
  a hydrocarbon chain, saturated or unsaturated, linear or branched comprising 1 to 6 carbon atoms;

$R_3$ and $R_4$ represent independently of each other:
  a hydrogen,
  a phenyl or benzyl group, optionally substituted on the phenyl ring by:
    1 to 5 halogen atoms notably fluorine or bromine,
    a OH, SH, OR" or SR", R" radical having the same definition as previously recited,
    an amino group, optionally mono- or di-substituted by an aliphatic group, cyclic or linear, with 1 to 6 carbon atoms,
    a trifluoromethyl group,
    an aromatic or heteroaromatic group with 5 or 6 atoms,
  a heteroaromatic group with 5 or 6 atoms, containing 1 or 2 heteroatom(s) taken from oxygen, nitrogen or sulphur, the sulphur and nitrogen atoms being able to be oxidized in S-oxide or N-oxide form, or
  a methylene substituted by a heterocycle with 5 or 6 atoms, aromatic or saturated, the heteroatom being oxygen, nitrogen or sulphur, the nitrogen and sulphur atoms being able to be oxidized in N-oxide or S-oxide form;

$R_3$ and $R_4$ do not simultaneously represent a hydrogen atom;

$R_5$ and $R_6$ represent independently of each other:
  a hydrogen atom, or
  a hydrocarbon chain, saturated or unsaturated, linear or branched with 1 to 6 carbon atoms and;

$R_7$ represents:
  a hydrogen,
  a $CH_2COOR'''$ or $CH(CH_3)COOR'''$ radical, R''' representing;
    a saturated hydrocarbon chain with 1 to 6 carbon atoms, optionally substituted by a $C_1$ to $C_3$ alkoxy group,
    a $C_5$ to $C_8$ cycloalkyl group,
    a phenyl, benzyl, heteroaromatic or heteroaromatic alkyl group, or
    a CH(R)O—C(O)OR' or CH(R)OC(O)R' group in which R and R' have the same definitions as previously recited.

2. The method according to claim 1, being associated with improving a process of eye healing and/or eye cicatrisation.

3. The method according to claim 1, being associated with preventing neovascularisation, preventing an onset of a toxic keratopathy, of problems at a level of an epithelium or permanent scars, or preventing or treating eye inflammation linked to keratitis, scleritis, episcleritis, uveitis, a cataract, a synechia, a macular oedema, a detachment of the retina, an ocular hypertension and degeneration of the optic nerve caused by glaucoma.

4. The method according to claim 1, wherein in the compound of formula (I), $R_1$ represents an (acyloxy)alkyl carbamate —C(=O)—O—C(R)(R')—OC(=O)—R" group.

5. The method according to claim 1, wherein in the compound of formula (I), $R_1$ represents a —C(=O)—O—CHMe-OC(=O)—CHMe$_2$ group.

6. The method according to claim 1, wherein in the compound of formula (I), $R_3$ represents a hydrogen atom.

7. The method according to claim 1, wherein in the compound of formula (I), $R_4$ represents a benzyl group optionally substituted by 1 to 5 halogen atom(s), a phenyl or a 5 or 6 membered heteroaromatic group.

8. The method according to claim 1, wherein in the compound of formula (I), $R_5$ represents a hydrogen atom.

9. The method according to claim 1, wherein in the compound of formula (I), $R_6$ represents an alkyl group.

10. The method according to claim 1, wherein in the compound of formula (I), $R_7$ represents a hydrogen atom.

11. The method according to claim 1, wherein the compound of formula (I), is selected from the following compounds:
Benzylic ester of 2-(2-biphenyl-4-ylmethyl-3-{hydroxy-[1-(1-isobutyryloxy-ethoxycarbonylamino)-ethyl]-phosphinoyl}-propionylamino)-propionic acid,
2-(2-Biphenyl-4-ylmethyl-3-{hydroxy-[1-(1-isobutyryloxy-ethoxycarbonylamino)-ethyl]-phosphinoyl}-propionylamino)-propionic acid,
Ethyl ester of 2-(2-biphenyl-4-ylmethyl-3-{hydroxy-[1-(1-isobutyryloxy-ethoxycarbonylamino)-ethyl]-phosphinoyl}-propionylamino)-propionic acid,
Ethoxycarbonyloxy ester of 2-(2-biphenyl-4-ylmethyl-3-{hydroxy-[1-(1-isobutyryloxy-ethoxycarbonylamino)-ethyl]-phosphinoyl}-propionylamino)-propionic acid,
Benzylic ester of 2-(2-(4-bromo-benzyl)-3-{hydroxy-[1-(1-isobutyryloxy-ethoxycarbonylamino)-ethyl]-phosphinoyl}-propionylamino)-propionic acid,
2-(2-(4-Bromo-benzyl)-3-{hydroxy-[1-(1-isobutyryloxy-ethoxycarbonylamino)-ethyl]-phosphinoyl}-propionylamino)-propionic acid,
Benzylic ester of 2-(2-biphenyl-4-ylmethyl-3-{hydroxy-[1-(amino)-ethyl]-phosphinoyl}-propionylamino)-propionic acid,
2-(2-Biphenyl-4-ylmethyl-3-{hydroxy-[1-(amino)-ethyl]-phosphinoyl}-propionylamino)-propionic acid,
Ethyl ester of 2-(2-biphenyl-4-ylmethyl-3-{hydroxy-[1-(1amino)-ethyl]-phosphinoyl}-propionylamino)-propionic acid,
Ethoxycarbonyloxy ester of 2-(2-biphenyl-4-ylmethyl-3-{hydroxy-[1-(amino)-ethyl]-phosphinoyl}-propionylamino)-propionic acid,
Benzylic ester of 2-(2-(4-bromo-benzyl)-3-{hydroxy-[1-(amino)-ethyl]-phosphinoyl}-propionylamino)-propionic acid,
2-(2-(4-Bromo-benzyl)-3-{hydroxy-[1-(amino)-ethyl]-phosphinoyl}-propionylamino)-propionic acid, and
Ethyl ester of 2-(2-(4-bromo-benzyl)-3-{hydroxy-[1-(amino)-ethyl]-phosphinoyl}-propionylamino)-propionic acid.

12. A method for treating or preventing eye inflammation in a subject in need thereof, the method comprising administering an ophthalmic composition including a compound of formula (I) comprising:

in which:
$R_1$ represents:
  a hydrogen, or
  an (acyloxy)alkyl carbamate —C(=O)—O—C(R)(R')—OC(=O)—R" group in which R and R' represent, independently of each other, a hydrogen, an alkyl group and R" represents an alkyl group;
$R_2$ represents:
  a hydrocarbon chain, saturated or unsaturated, linear or branched comprising 1 to 6 carbon atoms;
$R_3$ and $R_4$ represent independently of each other:
  a hydrogen,
  a phenyl or benzyl group, optionally substituted on the phenyl ring by:
    1 to 5 halogen atoms notably fluorine or bromine,
    a OH, SH, OR" or SR", R" radical having the same definition as previously recited,
    an amino group, optionally mono- or di-substituted by an aliphatic group, cyclic or linear, with 1 to 6 carbon atoms,
    a trifluoromethyl group,
    an aromatic or heteroaromatic group with 5 or 6 atoms,
  a heteroaromatic group with 5 or 6 atoms, containing 1 or 2 heteroatom(s) taken from oxygen, nitrogen or sulphur, the sulphur and nitrogen atoms being able to be oxidized in S-oxide or N-oxide form, or
  a methylene substituted by a heterocycle with 5 or 6 atoms, aromatic or saturated, the heteroatom being oxygen, nitrogen or sulphur, the nitrogen and sulphur atoms being able to be oxidized in N-oxide or S-oxide form;
$R_3$ and $R_4$ do not simultaneously represent a hydrogen atom;
$R_5$ and $R_6$ represent independently of each other:
  a hydrogen atom, or
  a hydrocarbon chain, saturated or unsaturated, linear or branched with 1 to 6 carbon atoms and;
$R_7$ represents:
  a hydrogen,
  a CH$_2$COOR''' or CH(CH$_3$)COOR''' radical, R''' representing:
    a saturated hydrocarbon chain with 1 to 6 carbon atoms, optionally substituted by a $C_1$ to $C_3$ alkoxy group,
    a $C_5$ to $C_8$ cycloalkyl group,
    a phenyl, benzyl, heteroaromatic or heteroaromatic alkyl group, or
  a CH(R)O—C(O)OR' or CH(R)OC(O)R' group in which R and R' have the same definitions as previously recited.

13. The method according to claim 12, wherein the ophthalmic composition includes 0.01% to 3% in weight by volume of the compound of formula (I).

14. The method according to claim 12, wherein the ophthalmic composition is an aqueous solution.

15. The method according to claim 12, wherein the ophthalmic composition further includes a cyclodextrin, or sodium polystyrene sulphonate.

16. The method according to claim 1, wherein the subject in need thereof is a human.

17. The method according to claim 7, wherein in the compound of formula (I), $R_4$ represents a benzyl group optionally substituted by a phenyl.

18. The method according to claim 12, wherein the ophthalmic composition is eye lotion, ophthalmic ointment, ophthalmic gel or ophthalmic insert.

19. The method according to claim 13, wherein the ophthalmic composition includes 0.1% to 1% in weight by volume of the compound of formula (I).

20. The method according to claim 14, wherein the ophthalmic composition has a pH ranging from 5.0 to 8.

* * * * *